United States Patent [19]

Fournial et al.

[11] Patent Number: 4,686,995
[45] Date of Patent: Aug. 18, 1987

[54] ELECTROCARDIOGRAM ELECTRODE APPARATUS

[76] Inventors: Jean-François Fournial, La Sauvagere, Route de Parinier, 72560 Change; Gilles Ascher, 20bis, Boulevard du Général Leclerc, 92200 Neuilly-sur-Seine, both of France

[21] Appl. No.: 828,298

[22] Filed: Feb. 11, 1986

[51] Int. Cl.⁴ ............................................. A61B 5/04
[52] U.S. Cl. .................................................. 128/640
[58] Field of Search .............................. 128/639–641, 128/643, 644, 798, 802, 803

[56] References Cited

U.S. PATENT DOCUMENTS

| | | | |
|---|---|---|---|
| 3,545,432 | 12/1970 | Berman | 128/640 |
| 4,040,412 | 8/1977 | Sato | 128/640 |
| 4,383,529 | 5/1983 | Webster | 128/802 X |
| 4,556,066 | 12/1985 | Semrow | 128/640 X |

Primary Examiner—Lee S. Cohen
Attorney, Agent, or Firm—Bachman & LaPointe

[57] ABSTRACT

The present invention provides electrode apparatus for use in taking electrocardograms (ECGs) in ambulatory mode according to the Holter method. The apparatus includes a metal electrode comprising a disc and a stud to which a flexible electrical condutor is connected. A flexible sponge disc is fitted over the stud, the disc having an adhesive-coated lower face, whereby to secure the disc and the electrode to the patient's skin. To protect the electrode from shocks and from pulls on the conductor, it is covered with a cup-shaped cover member presenting a base a side wall and a flange. The bottom surface of the flange is coated with adhesive whereby it is secured to the patient's skin with the electrode, disc, and a slack portion of the conductor within it.

4 Claims, 3 Drawing Figures

U.S. Patent  Aug. 18, 1987  4,686,995 and for adhering to the sponge ring 7 which becomes impregnated with the adhesive.

ELECTROCARDIOGRAM ELECTRODE APPARATUS

BACKGROUND OF THE INVENTION

This invention relates to electrode apparatus for use in taking electrocardiograms (E.C.Gs) in monitoring or ambulatory modes according to the Holter method, in which the heart beat of a patient is recorded for a long period, of 24 hours for example.

In this process, electrodes are applied directly to the patients body and form pick-ups connected to a portable recorder apparatus which may record continuously all the variations in heart beat occurring during a complete day of normal activity of the patient.

DESCRIPTION OF THE PRIOR ART

In a previous apparatus of this kind, the electrodes are disposable and each electrode comprises a metallic member whose lower part is disc-shaped for application to the patient's skin, and whose upper part comprises a stud having a circular radial groove in which is fixed the end of a flexible conductor which is connected to the recorder apparatus.

The disc part of the electrode is covered by a larger diameter disc in flexible sponge material through a central aperture of which projects the stud terminal. The sponge disc has an adhesive layer on the outer part of its lower face by which the electrode may be secured to the patient's skin.

The conductor is secured to the stud of the electrode by means of a metal clip in the form of a split ring or a pincer.

It is important that while the patient is wearing the electrodes the conductors connected to the electrodes should not be moved accidentally by unintentional pulling. Also it is important that the electrode itself should not be knocked or pulled off by accidental rubbing.

Experience has shown that the electrodes and the conductors connected to them are subjected to various accidental forces tending to move them and even pull them off.

The shocks pulls and movements which they undergo generate parasitic voltages which are in fact recorded on the ECG by the recorder apparatus and hinder considerably the reading of the ECG.

The ECG may in fact be read by automatic apparatus which is not capable of distinguishing accidental parasitic voltages and eliminate them to provide a cleansed curve. Otherwise, direct reading by the doctor, which is an extremely long operation, is also made very difficult because of the parasitic voltages.

It is known to fix the conductors to the patient's skin at a certain distance from the electrode by means of pieces of suitable adhesive tape, the electrode being fixed as before by the adhesive of the sponge disc which secures it to the patient's body, but this is rather ineffective and also inconvenient.

OBJECTS OF THE INVENTION

An object of the invention is to reduce or prevent the incidence of artefacts which may hide pathologically significant features of the ECG.

Another object of the invention is to protect the electrodes and conductors.

BRIEF DESCRIPTION OF THE INVENTION

The present invention provides an electrode apparatus for use in taking electrocardiograms in an ambulatory mode, comprising a metal electrode member presenting an electrode disc and a stud projecting from said disc for connection with an electrical conductor, a flexible adhesive disc defining a central aperture for fitting over said stud and presenting an adhesive-coated face by which said adhesive disc and electrode disc may be secured to the patient's skin, and a cover member for covering said electrode member, said adhesive disc and a part of said conductor, said cover member presenting a base portion, a side wall portion depending from said base portion, and presenting a substantially planar edge, and a flange extending from said edge generally in the same plane as said edge when unstressed, said flange portion bearing a coating of contact adhesive on a face thereof opposite to said base, whereby said cover member may be secured to the patient's skin with said electrode member, said adhesive disc and said part of said conductor within it, said conductor being trapped between said adhesive coating and the patient's skin.

In a preferred embodiment of the invention, said cover member comprises a deformable and translucent plastics material.

Preferably, said flange is formed integrally with said side wall portion and said base portion.

Advantageously, said cover member is a hot-formed member.

Alternatively, said cover member is a moulded member.

DESCRIPTION OF THE DRAWINGS

Other features and advantages of the invention will appear from the following description, given by way of example, with reference to the accompanying drawings, in which.

DESCRIPTION OF PREFERRED EMBODIMENTS OF THE INVENTION

Figure 1:
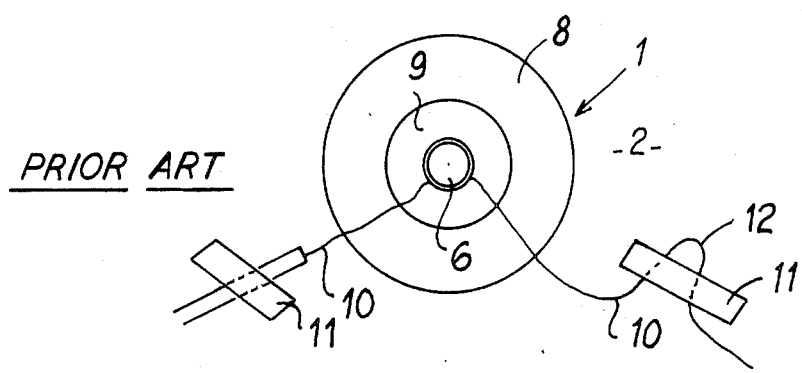
FIG. 1 is a schematic diagram showing an electrode and conductors fixed to a patient in accordance with a prior art design.

In the prior art apparatus shown in FIG. 1, an electrode 1 is fixed directly to the skin 2 of a patient the shape of the electrode being similar to the male part of a press-stud fastener.

Figure 2:
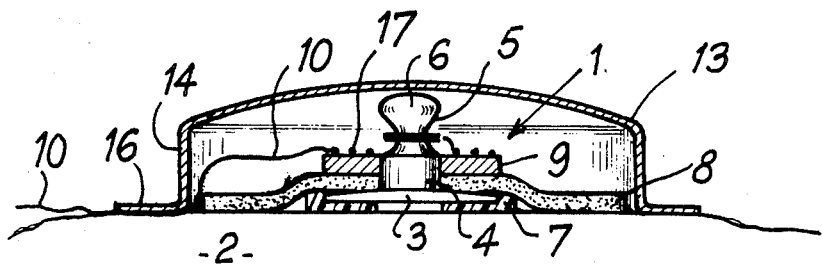
FIG. 2 is an elevational sectional view of an electrode apparatus in accordance with the present invention.

In accordance with the prior art and the present invention, and as shown in more detail in FIG. 2, the apparatus includes a disc 3 having a planar lower face and a stud 4 projecting from its upper face, the stud 4 presenting a peripheral groove 5 and a head 6. A ring 7 is fixed to the periphery of the disc 3, the ring 7 comprising a plastics sponge material impregnated with an electrically conductive liquid, and a disc 8 also in sponge material and having a central aperture is fitted on the stud 4 so that the stud projects through the central aperture.

The sponge disc 8 is flexible and on its face opposite to the projection of the stud 4 it presents a layer of contact adhesive for adhering the disc to the skin 2.

A washer 9 of relatively rigid material comprises a central aperture of a size suitable for force-fitting on the stud 4 so as to maintain the disc 8 pressed against the upper face of the disc 3 of the electrode.

As shown in FIG. 1, the apparatus includes a flexible conductor 10 connected to the electrode 1 by the groove 5 and, in the prior art apparatus, the conductor 10 was secured to the patient's skin 2 by pieces of suitable adhesive tape 11, such as "scotch" tape or "sparadrap" tape.

Although the conductor was generally arranged to describe a loop 12 which gave some play in case of accidental pulling on its free stretch, unintentional displacements and rubbing to which the electrode itself was exposed gave rise to parasitic voltages which were extremely detrimental to reading the recording made, whether by automatic means or direct reading by a specialist.

Figure 3:
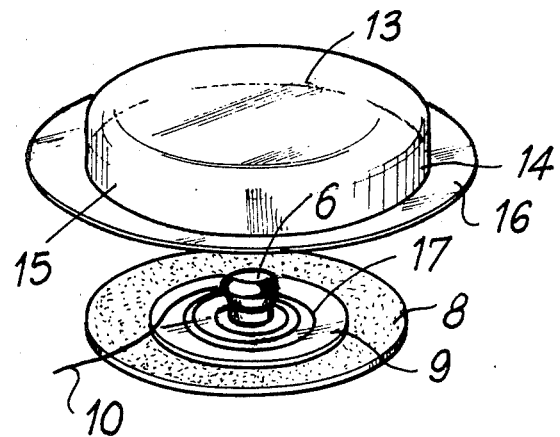
FIG. 3 is an exploded perspective view of the electrode apparatus of FIG. 2 with a conductor connected thereto.

To avoid this problem, this embodiment of the invention includes a protection and safety device, as shown in FIGS. 2 and 3, and comprising a cap or cup having a base 13 which is advantageously arched, a side wall 14 depending from the base 13 and terminating in a planar edge 15 and a flange 16 solid with the edge 15 and extending in the same plane.

The surface of the flange 16 opposite to the projection formed by the parts 13 and 14 of the cap is covered with a layer of contact adhesive whereby the cap may be adhered to the patient's skin 2.

In the example illustrated, the conductor 10 is fixed to the groove 5 of the stud 4 by means of a spring clip, and is preferably coiled around the stud in a spiral 17 resting freely on the washer 9, the stretch of the conductor 10 which extends out of the cup being trapped between the lower adhesive-coated surface of the flange and the patient's skin.

It will be appreciated that the spiral 17, or other shapes of coil, provide slack so that if a pull is inadvertently exerted on the conductor 10, the conductor can play round the stud of the electrode without transferring the pull to the electrode. Moreover, the head 6 of the electrode is shielded by the arched base 13 from shocks and friction which would produce detrimental parasitic voltages.

The electrode is maintained adhering to the skin of the patient by the disc 8 covered with adhesive and a certain play is preferably provided between the outer edge of the disc 8 and the inner face of the side wall 14 to accommodate the elasticity of the patient's skin.

The cap 13, 14, 15, 16 used in this embodiment of the invention is made advantageously in a suitable flexible plastics material, for example polycarbonate and is sufficiently distortable to fit on any desired part of the body, the cap being made by hot deformation of moulding. The material used may be transparent or translucid so as to facilitate its positioning over the electrode with constant play round the electrode.

We claim:

1. Electrode apparatus for use in taking electrocardiograms in an ambulatory mode, comprising a metal electrode member presenting an electrode disc and a stud projecting from said disc for connection with an electrical conductor, a flexible adhesive disc defining a central aperture positively fitting over said stud and presenting an adhesive-coated face by which said adhesive disc and electrode disc may be secured to the patient's skin, and a cover member for covering said electrode member, said adhesive disc and a part of said conductor, said cover member presenting a base portion, a side wall portion depending from said base portion and presenting a substantially planar edge, and a flange extending from said edge generally in the same plane as said edge when unstressed, said flange portion bearing a coating of contact adhesive on a face thereof opposite to said base, whereby said cover member may be secured to the patient's skin with said electrode member, said adhesive disc and said part of said conductor within it, said conductor being trapped between said adhesive coating and the patient's skin.

2. Electrode apparatus as claimed in claim 1, wherein said cover member comprises a deformable and translucent plastics material.

3. Electrode apparatus as claimed in claim 2, wherein said flange is formed integrally with said side wall portion and said base portion.

4. Electrode apparatus as claimed in claim 1, wherein said cover member comprises polycarbonate material.

* * * * *